US009322742B2

United States Patent
Miyai et al.

(10) Patent No.: US 9,322,742 B2
(45) Date of Patent: Apr. 26, 2016

(54) HYDROGEN FLAME IONIZATION TYPE EXHAUST GAS ANALYZER

(71) Applicant: HORIBA, Ltd., Kyoto (JP)

(72) Inventors: Masaru Miyai, Kyoto (JP); Hiroshi Nakamura, Kyoto (JP); Masahiro Nishikawa, Kyoto (JP)

(73) Assignee: HORIBA, LTD., Kyoto (JP)

( * ) Notice: Subject to any disclaimer, the term of this patent is extended or adjusted under 35 U.S.C. 154(b) by 391 days.

(21) Appl. No.: 13/917,266

(22) Filed: Jun. 13, 2013

(65) Prior Publication Data

US 2013/0333443 A1  Dec. 19, 2013

(30) Foreign Application Priority Data

Jun. 14, 2012  (JP) .................... 2012-134619

(51) Int. Cl.
*G01M 15/10* (2006.01)
*G01N 27/62* (2006.01)
*G01N 30/68* (2006.01)

(52) U.S. Cl.
CPC ........... *G01M 15/102* (2013.01); *G01N 27/626* (2013.01); *G01N 30/68* (2013.01)

(58) Field of Classification Search
CPC ..... G01N 27/626; G01N 21/72; G01N 30/68; G01M 15/102
USPC ........................................................ 73/23.31
See application file for complete search history.

(56) References Cited

U.S. PATENT DOCUMENTS

| 3,460,910 A | 8/1969 | Emich | |
| 4,896,526 A | 1/1990 | Ratfisch | |
| 5,073,753 A * | 12/1991 | Collings | G01N 27/626 324/464 |
| 5,239,492 A * | 8/1993 | Hartwig | G01N 33/0006 702/27 |
| 6,238,622 B1 * | 5/2001 | Salimian | G01N 27/626 422/54 |
| 7,328,606 B2 * | 2/2008 | Nakamura | G01M 15/102 73/114.71 |
| 7,454,950 B2 * | 11/2008 | Nakamura | G01N 33/0032 73/23.31 |

(Continued)

FOREIGN PATENT DOCUMENTS

| JP | 52-093586 U | 7/1977 |
| JP | 04-034446 Y | 8/1992 |
| JP | 08-240564 A | 9/1996 |
| JP | 2002-310910 | 10/2002 |
| JP | 2007205968 | 8/2007 |
| JP | 2008-304213 A | 12/2008 |
| JP | 2010-281668 A | 12/2010 |

OTHER PUBLICATIONS

Wikipedia: "Input Offset Voltage", URL:http://en.wikipedia.org/wiki/Input_off_set_voltage, retrieved on Sep. 19, 2013.
Office Action dated Feb. 24, 2015 issued for Japanese patent application No. 2012-134619, 4 pgs.
Garthe, C. et al, HC Measurements by Means of Flame Ionization: Background and Limits of Low Emission Measurement, SAE transactions, 2003, vol. 112, No. 4, pp. 250-264.

*Primary Examiner* — Freddie Kirkland, III
(74) *Attorney, Agent, or Firm* — Brooks Kushman P.C.

(57) ABSTRACT

The present invention is intended to be able to determine an appropriate purge time in a hydrogen flame ionization type exhaust gas analyzer and a system incorporating the analyzer which includes: a collector electrode for capturing ions generated from exhaust gas by hydrogen flame; an acquisition circuit adapted to acquire ion current caused by the ions captured by the collector electrode; and an abnormality determining part for determining an abnormality in the case where a difference between a first output value of the acquisition circuit in the case where there flows no ion current caused by the exhaust gas to the collector electrode and a second output value of the acquisition circuit in the case where zero gas is introduced into the hydrogen flame is equal to a predetermined value.

5 Claims, 6 Drawing Sheets

(56) References Cited

U.S. PATENT DOCUMENTS 7,704,748 B2* 4/2010 Schaeffer ............... G01N 25/28
422/12
8,421,470 B2* 4/2013 Kitano ................... G01N 27/68
324/464
2006/0222563 A1* 10/2006 Nakamura ........... G01N 27/626
422/53
2006/0236752 A1 10/2006 Nakamura
2015/0054521 A1* 2/2015 Horiike ................. G01N 27/70
324/464

* cited by examiner

HYDROGEN FLAME IONIZATION TYPE EXHAUST GAS ANALYZER

CROSS-REFERENCE TO RELATED APPLICATION

This application claims priority to JP Application No. 2012-134619, filed on Jun. 14, 2012, the disclosure of which is incorporated in its entirety by reference herein.

TECHNICAL FIELD

The present invention relates to a hydrogen flame ionization type exhaust gas analyzer for measuring a concentration of a measurement target substance contained in the exhaust gas discharged from an internal combustion engine such as an engine of, for example, a vehicle and the like, or discharged from an external combustion engine such as a steam turbine.

BACKGROUND ART

As disclosed in JP2007-205968A, a hydrogen flame ionization detector (FID) of this kind is intended to detect ion current caused at a time of introducing a sample gas such as exhaust gas into hydrogen flame by a collector electrode to thereby measure a concentration of hydrocarbon which is a measurement target substance contained in the sample gas based on the ion current detected by the collector electrode. This hydrogen flame ionization detector is used while it is provided on an exhaust gas flow path in which the exhaust gas discharged from such as a vehicle.

Since hydrocarbon (for example, THC) contained in the exhaust gas is adhered to and deposited on an inner surface of an exhaust gas flow path incorporating the hydrogen flame ionization detector, an error component is to be contained in a concentration of hydrocarbon obtained by the hydrogen flame ionization detector. Therefore, conventionally, purge gas is supplied to the exhaust gas flow path and the hydrogen flame ionization detector by a predetermined regular purge process to thereby remove the adhered and deposited hydrocarbon.

However, in the case of performing a regular purge process as mentioned above, an amount of the hydrocarbon adhered to the exhaust gas flow path and the hydrogen flame ionization detector exceeds a permissible range in some cases even before performing a purge process. Then, the measurement of a concentration of a measurement target substance is to be performed remaining in a state of being incapable of addressing by such as a correction until the regular purge process is started.

Meanwhile, there may be a case where an amount of hydrocarbon adhered to the exhaust gas flow path and the hydrogen flame ionization detector is within a permissible range even without performing the regular purge process. In that case, a purge process of the exhaust gas flow path and the hydrogen flame ionization detector is to be performed as a lapse of a predetermined maintenance period, and there arises a problem such that a measurement should be necessarily stopped due to an unnecessary purge process.

SUMMARY

Technical Problem

Therefore, the present invention has been made in order to solve the problems at a stroke and its essential object is to be able to determine an appropriate purge time in a hydrogen flame ionization type exhaust gas analyzer and an exhaust gas analyzing system incorporating the hydrogen flame ionization type exhaust gas analyzer.

Solution to Problem

That is, a hydrogen flame ionization type exhaust gas analyzer according to the present invention is adapted to measure a concentration of a measurement target substance contained in the exhaust gas based on ion current that is generated upon introduction of the exhaust gas into hydrogen flame. The hydrogen flame ionization type exhaust gas analyzer is characterized by including: a collector electrode for capturing ions generated from the exhaust gas by the hydrogen flame; an acquisition circuit electrically connected to the collector electrode to acquire ion current caused by the ions captured by the collector electrode; and an abnormality determining part for determining an abnormality in the case where a difference between, a first output value outputted from the acquisition circuit in the case where there flows no ion current caused by the exhaust gas to the collector electrode or a first relevant value obtained from the first output value, and a second output value outputted from the acquisition circuit in the case where gas of a known concentration of a measurement target substance is introduced into the hydrogen flame or a second relevant value obtained from the second output value, is equal to or larger than a predetermined value. It is noted that the phrase "gas of a known concentration of a measurement target substance" implies a concept including the zero gas which does not contain a measurement target substance in addition to the gas containing a measurement target substance of a predetermined quantity.

With this configuration, since the abnormality is determined in the case where a difference between a first output value (or a first relevant value) outputted from the acquisition circuit in the case where there flows no ion current caused by the exhaust gas to the collector electrode and a second output value (or a second relevant value) outputted from the acquisition circuit in the case where gas of a known concentration of a measurement target substance is introduced into the hydrogen flame is equal to or larger than a predetermined value, it becomes possible to determine an appropriate purge time. The first output value (or first relevant value) outputted from the acquisition circuit in the case where there flows no ion current caused by the exhaust gas to the collector electrode is, in other words, a constant value irrespective of whether or not a measurement target substance adheres to the exhaust gas flow path and the hydrogen flame ionization type exhaust gas analyzer. Meanwhile, the second output value outputted from the acquisition circuit in the case where gas of a known concentration of a measurement target substance is introduced into the hydrogen flame is a value that increases in the case where the measurement target substance adheres to the exhaust gas flow path and the hydrogen flame ionization type exhaust gas analyzer. By taking a difference between these first and second output values, it becomes possible to determine how much degree of the measurement target substance is adhered to the exhaust gas flow path and the hydrogen flame ionization type exhaust gas analyzer, and hence an appropriate purge time can be determined.

In this configuration, it is considered that a voltage value obtained by current-to-voltage conversion of the first output value which is a current value, a digital signal obtained by A/D conversion of the first output value which is an analog signal, a value obtained by subjecting a predetermined calculation process such as, e.g., a linearity correction to the first output value, or the like may be available, as the first relevant value. Also, the second relevant value is the same as the first relevant value.

As the case where there flows no ion current caused by the exhaust gas to the collector electrode, there may be considered two cases: case (1) where the exhaust gas is not combusted by the hydrogen flame; and case (2) where a closed circuit for rendering current to flow into the collector electrode is interrupted. That is, it is considered that the first output value is outputted from the acquisition circuit in the case where the exhaust gas is not combusted by the hydrogen flame or in the case where the closed circuit for rendering the current to flow into the collector electrode is interrupted.

Here, as the case (1) where the exhaust gas is not combusted by the hydrogen flame, there may be considered two cases: (a) where the hydrogen flame has been turned off; and (b) where the exhaust gas is not introduced into the hydrogen flame. In the case of acquiring the first output value in the case (a) where the hydrogen flame has been turned off, it is only necessary to switch ignition (ON)/extinguishing (OFF) of the hydrogen flame. Also, in the case of acquiring the first output value in the case (b) where the exhaust gas is not introduced into the hydrogen flame, it is only necessary to switch introduction/stop of the exhaust gas to the hydrogen flame. Thus, there is no need to make a modification to the conventional configuration of the system. It is noted that, in the case (b), although there flows no ion current caused by the exhaust gas, the ion current flows to the collector electrode only by ignition of the hydrogen flame. Therefore, as the first output value, there may be used an output value in the case where the ion current caused by ignition of the hydrogen flame flows or may be used a value obtained by subtracting an output component caused by the ignition of the hydrogen flame from the above-mentioned output value.

Further, in the case of acquiring the first output value in the case (2) where the closed circuit for rendering the current to flow into the collector electrode is interrupted, a switching time can be made faster compared to the case of switching ignition/extinguishing of the hydrogen flame or switching introduction/stop of the exhaust gas, and it is also possible to increase a degree of freedom of the switching timing thereof.

Furthermore, it is preferable that the hydrogen flame ionization type exhaust gas analyzer includes a purge determining part for determining whether or not a purge output value obtained by the acquisition circuit in the case where purge gas is rendered to flow into an exhaust gas introduction path for introducing the exhaust gas into the hydrogen flame to introduce the purge gas into the hydrogen flame or a relevant value obtained from the purge output value, is smaller than a predetermined reference value. With this configuration, it is possible to determine appropriate end timing of the purge process. Therefore, by combining this merit with the above invention, it is possible to determine appropriate purge start timing and to determine appropriate end timing of the purge process, and hence it becomes possible to optimize the purge process in the hydrogen flame ionization type exhaust gas analyzer and the system incorporating the analyzer.

Advantageous Effects of Invention

According to the present invention configured as described above, it becomes possible to determine appropriate purge timing in the hydrogen flame ionization type exhaust gas analyzer and the system incorporating the analyzer.

DESCRIPTION OF EMBODIMENTS

The following describes one embodiment of a hydrogen flame ionization type exhaust gas analyzer according to the present invention with reference to the accompanying drawings.

Figure 1:
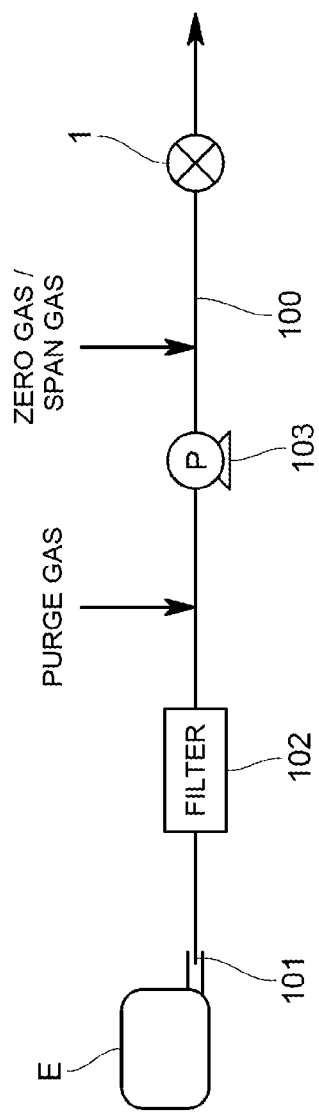
FIG. 1 is a schematic diagram showing a configuration of an exhaust gas analyzing system including a hydrogen flame ionization type exhaust gas analyzer of the present embodiment.

As shown in FIG. 1, a hydrogen flame ionization type exhaust gas analyzer 1 (referred to as "FID meter 1" hereinafter) of the present embodiment is provided on an exhaust gas flow path 100 with its one end connected to an introduction port 101 for introducing exhaust gas exhausted from an engine E. The FID meter 1 is adapted to measure a concentration of hydrocarbon which is an organic compound as a measurement target substance contained in the exhaust gas, based on ion current which is caused upon introduction of the exhaust gas into the hydrogen flame. Further, a filter 102 and a suction pump 103 etc. are provided on the exhaust gas flow path 100.

Figure 2:
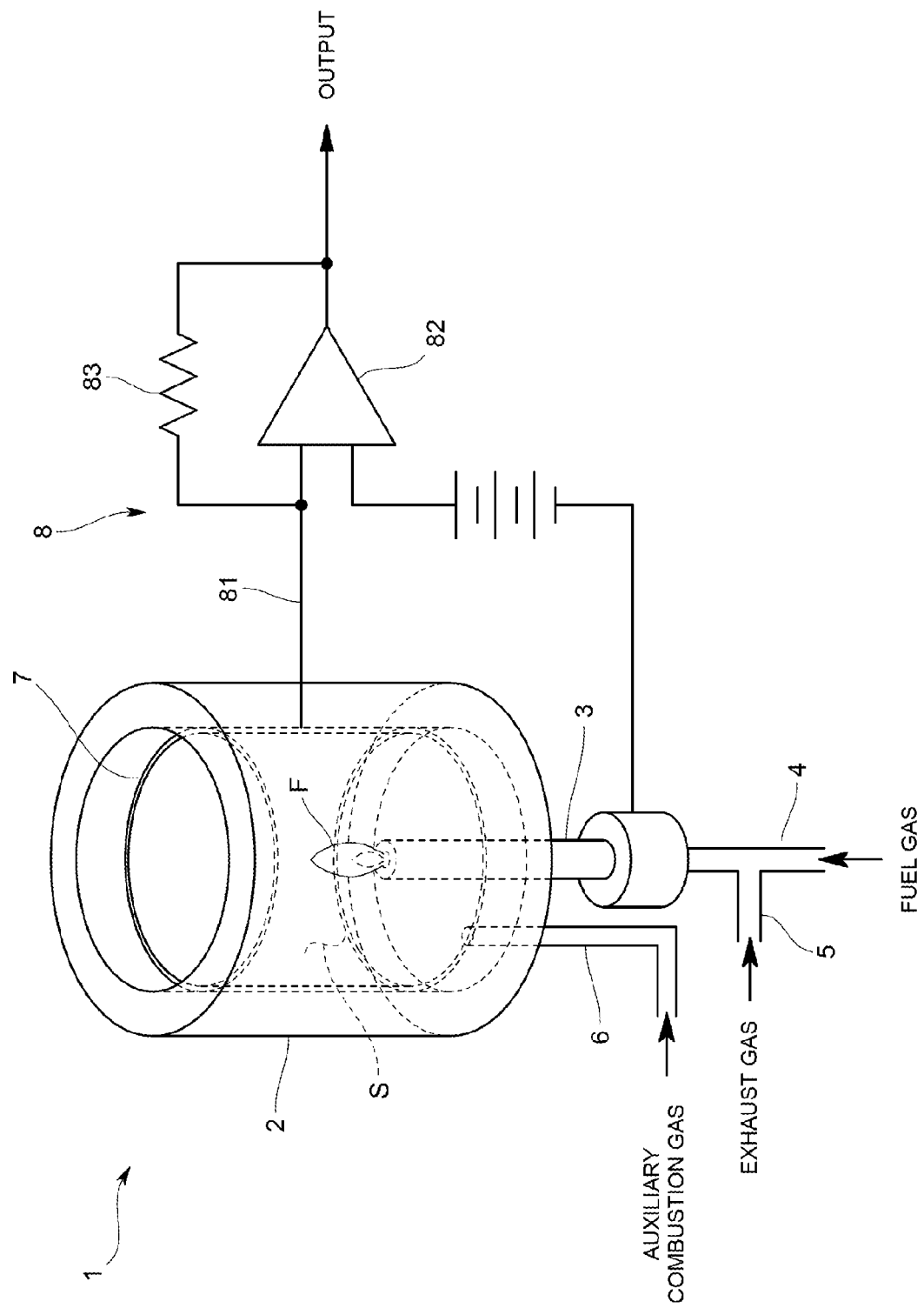
FIG. 2 is a schematic diagram showing a configuration of the hydrogen flame ionization type exhaust gas analyzer of the same embodiment.

Specifically, as shown in FIG. 2, the FID meter 1 includes a combustion chamber block (chimney) 2 having a combustion chamber S formed inside thereof and a nozzle 3 with its distal end portion provided inside the combustion chamber S for injecting hydrogen flame F. Further, a combustion gas supply path 4 for supplying the combustion gas to the nozzle 3 is connected to a proximal end portion of the nozzle 3. Further, an exhaust gas supply path 5 for supplying the exhaust gas from the exhaust gas flow path 100 together with the combustion gas to the nozzle 3 is connected to the combustion gas supply path 4. In addition, the FID meter 1 includes an auxiliary combustion gas supply path 6 for supplying auxiliary combustion gas (i.e., air) to the combustion chamber S.

Moreover, the FID meter 1 includes: a collector electrode 7 which is provided around the hydrogen flame F inside the combustion chamber S to capture the ions generated from the exhaust gas by the hydrogen flame F; an acquisition circuit 8 which is electrically connected to the collector electrode 7 to acquire the ion current which is caused upon capture of the ions by the collector electrode 7; and a calculation device 9 which acquires an output signal of the acquisition circuit 8 to calculate a concentration of hydrocarbon contained in the exhaust gas.

The acquisition circuit 8 includes: a lead wire 81 which is connected to the collector electrode 7; and an amplifier (operational amplifier) 82 which is connected to the lead wire 81 to amplify the ion current flowing through the collector electrode 7 and output the amplified ion current. In this arrangement, a feedback resistor 83 is connected between a minus-side input terminal and an output terminal of the amplifier 82.

Figure 3:
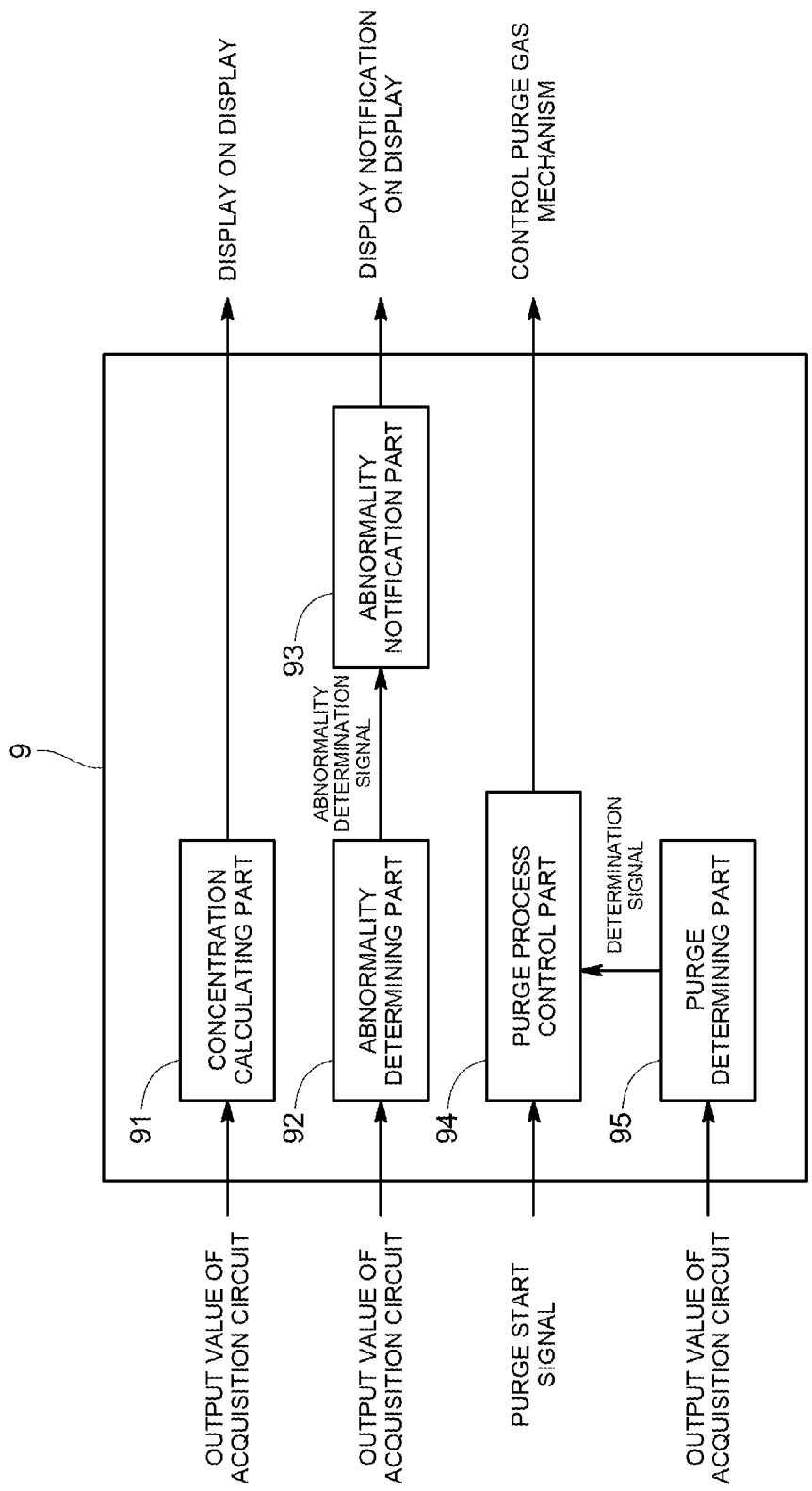
FIG. 3 is a block diagram showing a functional configuration of a computing device of the same embodiment.

The calculation device 9 is configured of a general purpose or dedicated computer including a CPU, an internal memory, an input/output interface, an A/D converter, a display, and the like. Specifically, as shown in FIG. 3, the calculation device 9 has a function as a concentration calculation portion 91 calculating a concentration of hydrocarbon (in specific, a THC concentration) contained in the exhaust gas based on the output signal outputted from the acquisition circuit 8. It is noted here that a value of the output signal is proportional to the concentration of the hydrocarbon contained in the exhaust gas.

Figure 4:
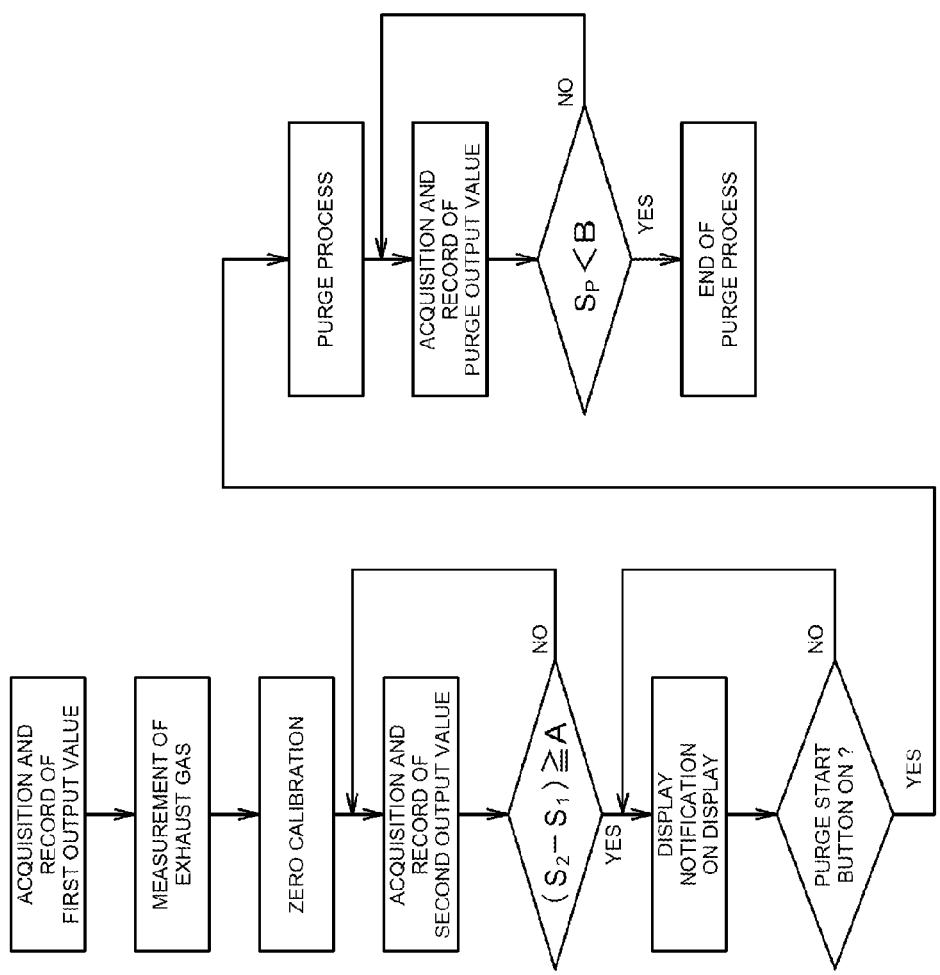
FIG. 4 is a flow chart showing a procedure of an abnormality determination and purge processing of the same embodiment.

Moreover, as shown in FIG. 3, the calculation device 9 has a function as an abnormality determining part 92 determining whether or not a predetermined amount or more of the hydrocarbon is adhered to the exhaust gas flow path 100 provided with the FID meter 1 and to the inside of the FID meter 1 in an abnormal state. FIG. 4 is a flow chart showing an example of a procedure from the abnormality determining process to a purge process.

Figure 5:
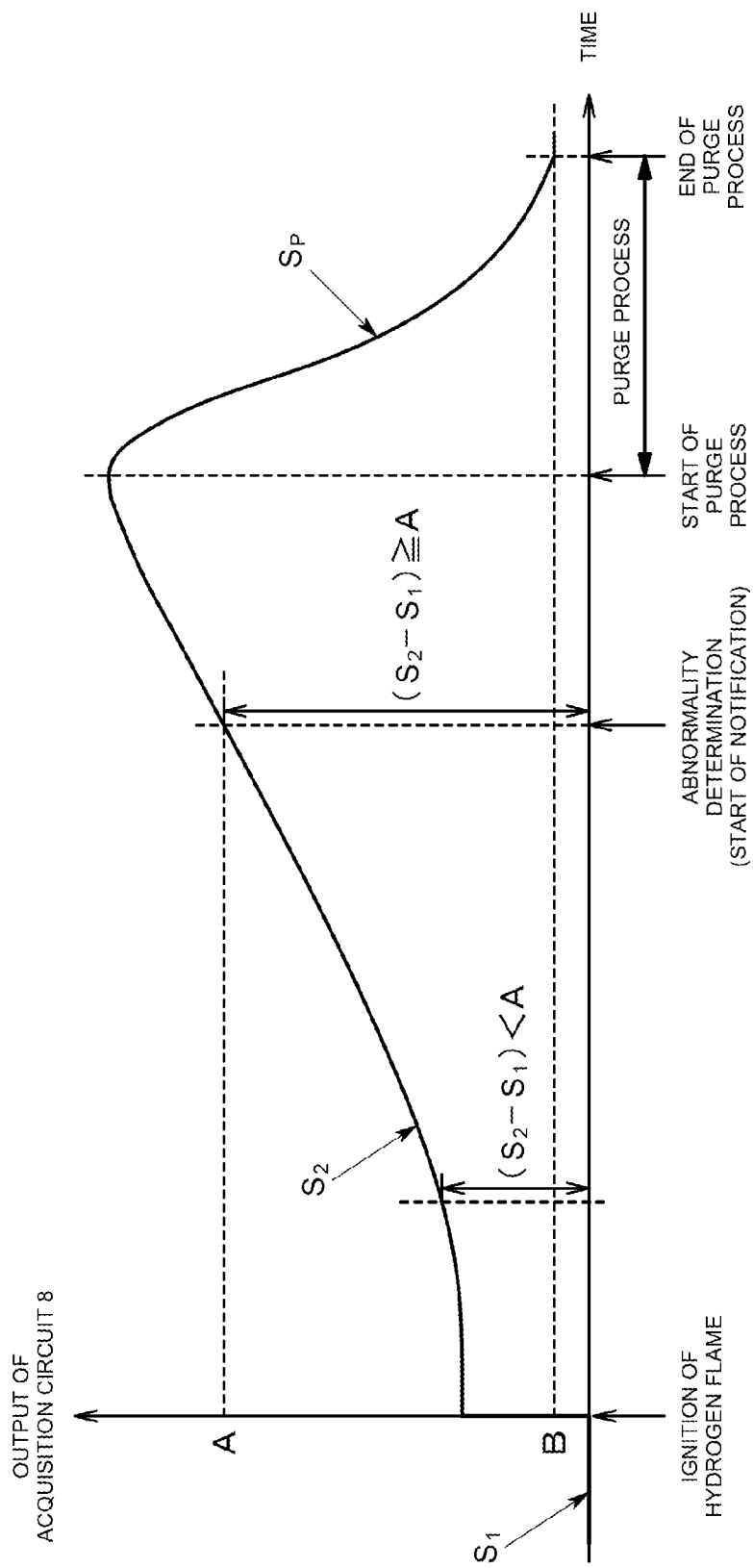
FIG. 5 is a schematic diagram showing a variation with time of an output value in the hydrogen flame ionization type exhaust gas analyzer.

As shown in FIG. 5, the abnormality determining part 92 determines whether or not a difference $(S_2-S_1)$ between, a first output value $S_1$ outputted from the acquisition circuit 8 in the case where there flows no ion current caused by the exhaust gas through the collector electrode 7, and, a second output value $S_2$ outputted from the acquisition circuit 8 in the case where gas of a known concentration of hydrocarbon (for example, zero gas having a zero concentration of hydrocarbon) is introduced into the hydrogen flame F, is equal to or larger than a predetermined threshold value A. In specific, the abnormality determining part 92 acquires the output value outputted from the acquisition circuit 8 as the first output value $S_1$ in the case where the exhaust gas is not combusted by the hydrogen flame F, i.e., in the case where the hydrogen flame F is being off. In the present embodiment, the first output value $S_1$ and second output value $S_2$ correspond to current signals (raw data) outputted from the acquisition circuit 8 before correction and before conversion in concentration, respectively.

In this arrangement, the first output value $S_1$ is, for example, an output value outputted from the acquisition circuit 8 at a time of shipping products of the FID meter 1 or before starting a first measurement of the FID meter 1, and the first output value $S_1$ is a value unique to the amplifier 82 of the acquisition circuit 8 and is a constant value regardless of whether the hydrocarbon substance is adhered to the exhaust gas flow path 100 or the FID meter 1. Thus, the first output value $S_1$ is acquired at a time of shipping products or before starting a first measurement of the FID meter 1, and is recorded in a recording part set in such as an internal memory or the abnormality determining part 92 of the calculation device 9. It is noted that, although the first output value $S_1$ may be sequentially acquired to be recorded, since it is outputted as a constant value in the case where the hydrogen flame F is turned off, it is sufficient to acquire the first output value $S_1$ to be recorded once at a time of shipping products or before starting a first measurement of the FID meter 1. Moreover, in the case where the amplifier 82 of the acquisition circuit 8 is replaced due to such as a maintenance thereof, the first output value $S_1$ is updated to a first output value $S_1$ unique to a substituted new amplifier 82.

In addition, the second output value $S_2$ is an output value which increases in accordance with increase of an amount of the hydrocarbon adhered to the exhaust gas flow path 100 and the FID meter 1. In the present embodiment, the second output value $S_2$ is an output value which is outputted from the acquisition circuit 8 in the case where measurement of exhaust gas is not performed. For example, in the case where a zero calibration, span calibration and measurement of exhaust gas of the FID meter 1 are performed in this order, the second output value $S_2$ is an output value outputted from the acquisition circuit 8 in a state that the zero calibration of the FID meter 1 is under performance. That is, the abnormality determining part 92 of the present embodiment does not perform an abnormality determination at the time of measurement of exhaust gas but performs the abnormality determination at the time of zero calibration. It is noted that, in the case where an output value outputted from the acquisition circuit 8 during a measurement of exhaust gas is used as the second output value $S_2$, the output value acquired during the measurement of exhaust gas results in containing an output component due to the hydrocarbon contained in the exhaust gas together with an output component due to contamination of such as deposited hydrocarbon other than that, it is impossible to take a correct target value by simply taking a difference $(S_2-S_1)$ between the first output value $S_1$ and the second output value $S_2$. In the present embodiment, although the second output value $S_2$ is acquired in the case where the zero gas is rendered to flow at the time of performing the zero calibration of the FID meter 1, it may be also acquired in the case where the zero gas is rendered to flow without performing the zero calibration.

Then, in the case where the difference $(S_2-S_1)$ between the first output value $S_1$ and the second output value $S_2$ is equal to or larger than the predetermined threshold value A, the abnormality determining part 92 outputs an abnormality determination signal indicative of the above abnormal state to an abnormality notification part 93.

This abnormality notification part 93 is configured by the calculation device 9 to be intended to notify a user that the difference $(S_2-S_1)$ is equal to or larger than the predetermined threshold value A, i.e., that a purge process of the exhaust gas flow path 100 and the FID meter 1 is required to be performed. The abnormality notification part 93 of the present embodiment is composed of a display control part performing a notification display on a display of the calculation device 9. Thus, the user can know that it is time to perform a purge process.

In this configuration, when the user presses a purge start button by such as seeing the notification display, a purge start signal receiving part (not shown) receives a purge start signal to thereby start a purge process by a purge process control part 94 which is configured by the calculation device 9.

More specifically, the purge process control part 94 controls a purge gas mechanism (not shown) which is configured of a purge gas supply path connected to the exhaust gas flow path 100, a purge gas pump and the like to thereby supply the purge gas to the exhaust gas flow path 100 and the FID meter 1.

In this purge process, the calculation device 9 has a function as a purge determining part 95 for appropriately determining purge end timing.

As shown in FIG. 5, in the case where the purge gas is rendered to flow through the exhaust gas introduction path for introducing the exhaust gas into the hydrogen flame F to thereby introduce the purge gas into the hydrogen flame F, the purge determining part 95 determines whether or not a purge output value $S_P$ acquired from the acquisition circuit 8 is smaller than a predetermined reference value B. In the case where the purge determining part 95 determines that a difference $(S_P-S_1)$ between the purge output value $S_P$ and the first output value $S_1$ is smaller than the predetermined reference value B, the purge determining part 95 outputs a corresponding determination signal to the purge process control part 94. Upon acquisition of this determination signal, the purge process control part 94 renders the purge process to be ended. It is noted that, in the case of strictly determining the purge end, although it is desirable to compare the difference ($S_P$-$S_1$) between the purge output value $S_P$ and the first output value $S_1$ with the predetermined reference value B, it is configured in the present embodiment to simply compare the purge output value $S_P$ with the predetermined reference value B.

According to the FID meter 1 according to the present embodiment configured as described above, since it is determined whether or not the difference ($S_2$-$S_1$) between the first output value $S_1$ outputted from the acquisition circuit 8 in the case where there flows no ion current through the collector electrode 7 and the second output value $S_2$ outputted from the acquisition circuit 8 in the case where zero gas is introduced into the hydrogen flame F, is equal to or larger than the predetermined threshold value A, it becomes possible to determine appropriate purge timing.

In addition, the present invention should not be limited to the above embodiment.

For example, although the acquisition circuit outputs the ion current amplified by the amplifier, the ion current before amplified by the amplifier may be used as the first output value and the second output value.

In addition, the abnormality determining part may be configured to determine an abnormality using a voltage value obtained by current-to-voltage converting the first output value (current value) outputted from the acquisition circuit as a first relevant value and a voltage value obtained by current-to-voltage converting the second output value (current value) as a second relevant value and taking a difference between the first and second relevant values to determine the abnormality based on the difference.

Moreover, the abnormality determining part may be configured to determine an abnormality based on a difference between first and second relevant values before converting to concentrations obtained by subjecting the first and second output values outputted from the acquisition circuit to a predetermined calculation process such as a correction. Further, digital values obtained by digitally converting the first and second output values may be used as the first and second relevant values. In this case, the acquisition circuit includes an A/D conversion circuit.

Further, by converting the first output value to a first concentration value which is used as a first relevant value and by converting the second output value to a second concentration value which is used as a second relevant value, the abnormality determination may be performed based on a difference between the first relevant value and the second relevant value.

In this configuration, in the case of performing the zero calibration as in the above embodiment, the second output value $S_2$ is referenced as a zero point. Therefore, with a configuration capable of setting the first output value $S_1$ as a minus concentration, by converting the first output value $S_1$ to a first concentration value which is used as a first relevant value and by converting the second output value $S_2$ to a second concentration value which is used as a second relevant value, the abnormality determining part may determine an abnormality based on the difference between the first relevant value and the second relevant value.

Further, in the present embodiment, although the purge process is started upon pressing of the purge start button by a user, the purge process may be automatically started in the case where the abnormality determining part 92 determines an abnormality.

Moreover, in the present embodiment, although the abnormality determining part, abnormality notification part, purge process control part and purge determining part are configured by the calculation device, these functions may be implemented by at least one control unit other than the calculation device. Also, these functions may be implemented in either the calculation device or the other control unit.

In addition, in the present embodiment, although an output value of the acquisition circuit 8 is used as the first output value in a state that the hydrogen flame F is being off (OFF time), an output value of the acquisition circuit 8 may be used as the first output value in a state that the hydrogen flame F is being ignited and the supply of the exhaust gas through the nozzle is being stopped.

Figure 6:
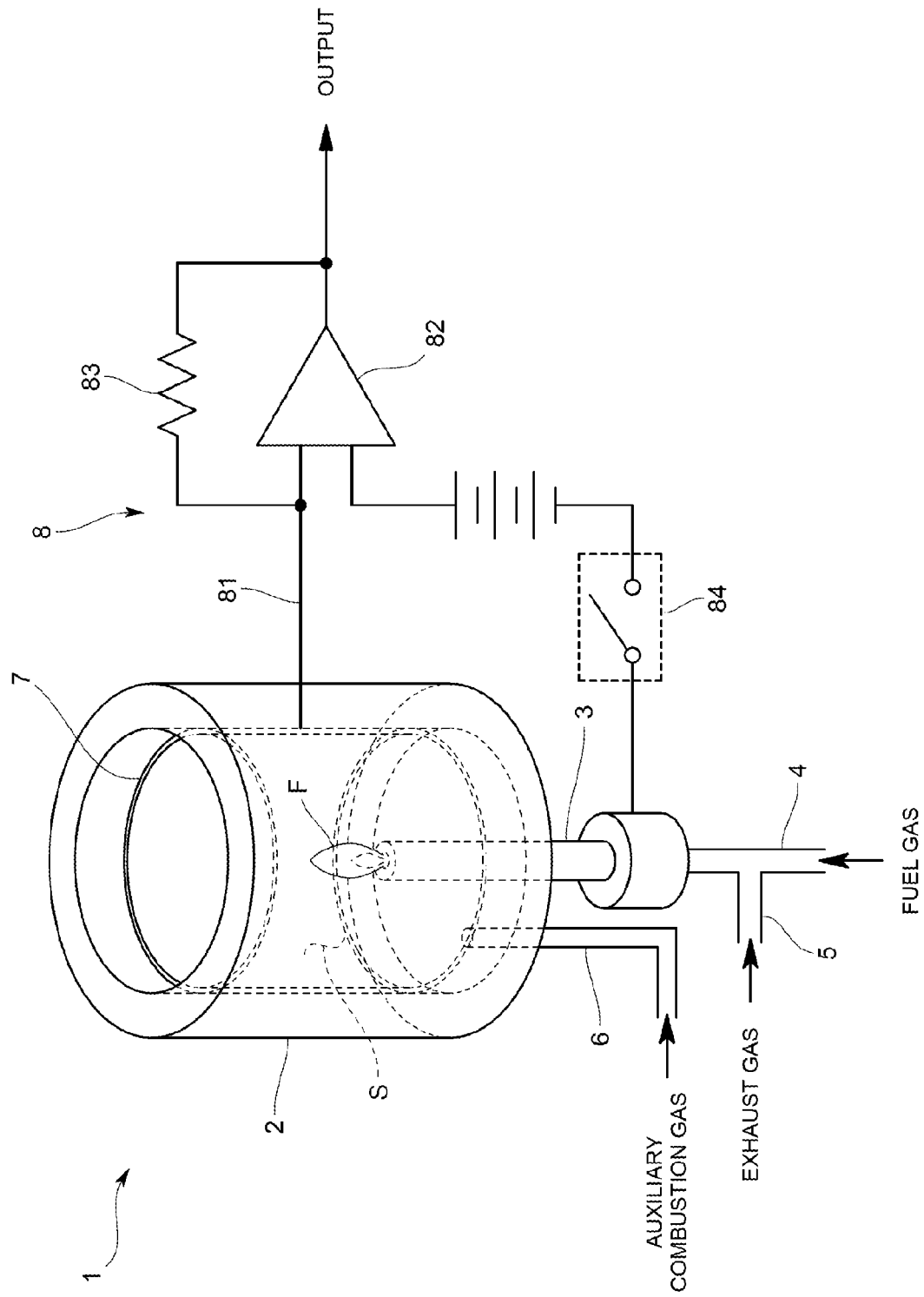
FIG. 6 is a schematic diagram showing a configuration of a hydrogen flame ionization type exhaust gas analyzer of a modified embodiment.

Furthermore, as shown in FIG. 6, the output value of the acquisition circuit 8 in the case where the closed circuit for flowing the current through the collector electrode 7 is interrupted, may be used as the first output value $S_1$. In specific, it may be considered that, an on/off switch 84 for interrupting the acquisition circuit 8 is provided in the acquisition circuit 8 to be a closed circuit and in the case where the on/off switch 84 is opened, the output value of the acquisition circuit 8 may be used as the first output value $S_1$.

Further, in the present embodiment, although an output value obtained in the case where the zero gas having a concentration of hydrocarbon being zero is rendered to flow is used as the second output value, a value obtained by subtracting an output value caused by hydrocarbon of the known concentration from an output value obtained in the case where gas containing hydrocarbon of the known concentration is rendered to flow may be used as the second output value. Further, an output value obtained in the case where the gas containing the hydrocarbon of a known concentration may be used as the second output value.

Moreover, the abnormality determining part may be configured to determine an abnormality without calculating a difference between the first and second output values in the case where the second output value outputted from the acquisition circuit in the case of introducing the gas of a known concentration of hydrocarbon into the hydrogen flame or the second relevant value obtained from the second output value is equal to or larger than a predetermined value. In this case, it may be considered that the predetermined value is set in consideration of the first output value.

In addition, the present invention should not be limited to the above embodiment, and various modifications are of course possible within the scope unless departing from the intended spirit thereof.

REFERENCE SIGNS LIST

1 . . . Hydrogen flame ionization type exhaust gas analyzer (FID meter)
F . . . Hydrogen flame
7 . . . Collector electrode
8 . . . Acquisition circuit
$S_1$ . . . First output value
$S_2$ . . . Second output value
92 . . . Abnormality determining part
95 . . . Purge determining part
$S_P$ . . . Purge output value While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A hydrogen flame ionization type exhaust gas analyzer adapted to measure a concentration of a measurement target substance contained in an exhaust gas based on ion current that is generated upon introduction of the exhaust gas into a hydrogen flame of the hydrogen flame ionization type exhaust gas analyzer, comprising:
 a collector electrode for capturing ions generated from the exhaust gas by the hydrogen flame;
 an acquisition circuit electrically connected to the collector electrode to acquire ion current caused by the ions captured by the collector electrode; and
 an abnormality determining part for determining an abnormality in the case where a difference between a first output value or a first relevant value obtained from the first output value, and a second output value or a second relevant value obtained from the second output value, is equal to or larger than a predetermined value, wherein the first output value is measured by the acquisition circuit while no ion current caused by the exhaust gas flows to the collector electrode and wherein the second output value is measured by the acquisition circuit while gas of a known concentration of a measurement target substance is introduced into the hydrogen flame.

2. The hydrogen flame ionization type exhaust gas analyzer according to claim 1, wherein during measurement of the first output value, no exhaust gas is combusted by the hydrogen flame.

3. The hydrogen flame ionization type exhaust gas analyzer according to claim 1, wherein during measurement of the first output value, a closed circuit for supplying current to the collector electrode is interrupted.

4. The hydrogen flame ionization type exhaust gas analyzer according to claim 1 further comprising a purge determining part for determining whether or not a purge output value or a relevant value obtained from the purge output value is smaller than a predetermined reference value, wherein the purge output value is measured by the acquisition circuit while purge gas flows into an exhaust gas introduction path for introducing the exhaust gas into the hydrogen flame to introduce the purge gas into the hydrogen flame.

5. A method for measuring a concentration of a measurement target substance contained in an exhaust gas by a hydrogen flame ionization type exhaust gas analyzer based on ion current that is generated upon introduction of the exhaust gas into a hydrogen flame of the hydrogen flame ionization type exhaust gas analyzer, comprising:
 capturing ions generated from the exhaust gas by the hydrogen flame with a collector electrode;
 acquiring an ion current caused by the ions captured by the collector electrode with an acquisition circuit electrically connected to the collector electrode;
 measuring by the acquisition circuit a first output value while no ion current caused by the exhaust gas flows to the collector electrode;
 measuring by the acquisition circuit a second output value while gas of a known concentration of a measurement target substance is introduced into the hydrogen flame; and
 determining with an abnormality determining part an abnormality in the case where a difference between the first output value or a first relevant value obtained from the first output value, and the second output value or a second relevant value obtained from the second output value, is equal to or larger than a predetermined value.

* * * * *